United States Patent
Bayer et al.

(10) Patent No.: US 6,942,785 B2
(45) Date of Patent: Sep. 13, 2005

(54) SYSTEM FOR AUTOMATED TREATMENT OF FLUIDS HAVING SUCCESSIVE AND INTERCHANGEABLE PROCESS MODULES

(75) Inventors: Thomas Bayer, Bad Soden (DE); Klaus-Dieter Fiebelkorn, Minfeld (DE); Axel Gerlt, Fuerth (DE); Joerg Hassel, Erlangen (DE); Richard Mateman, Enschede (NL); Arno Steckenborn, Berlin (DE); Jeroen Wissink, Enschede (NL)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/639,427

(22) Filed: Aug. 13, 2003

(65) Prior Publication Data
US 2004/0164010 A1 Aug. 26, 2004

Related U.S. Application Data (63) Continuation of application No. PCT/DE02/00504, filed on Feb. 2, 2002.

(30) Foreign Application Priority Data
Feb. 13, 2001 (DE) .......................................... 101 06 558

(51) Int. Cl.[7] .............................................. B01D 17/12
(52) U.S. Cl. ........................ 210/91; 137/270; 137/271; 137/553; 210/94; 210/143; 210/252; 210/541; 366/341; 422/103; 422/189
(58) Field of Search .............................. 210/198.2, 232, 210/252, 259, 541, 91, 94, 143; 137/269, 271, 553–555, 804, 270; 422/62, 63, 68.01, 102, 103, 188, 189; 366/341; 285/312

(56) References Cited

U.S. PATENT DOCUMENTS

| | | | |
|---|---|---|---|
| 3,934,605 A | * | 1/1976 | Legris ........................ 137/271 |
| 5,083,364 A | | 1/1992 | Olbrich et al. |
| 5,519,635 A | * | 5/1996 | Miyake et al. ............... 700/285 |
| 5,580,523 A | * | 12/1996 | Bard ............................ 422/50 |
| 5,766,460 A | | 6/1998 | Bergstrom et al. |
| 6,495,103 B2 | * | 12/2002 | Hettinger ................... 422/68.1 |

FOREIGN PATENT DOCUMENTS

| | | |
|---|---|---|
| DE | 199 54 855 C1 | 4/2001 |
| EP | 0 303 565 A1 | 2/1989 |
| EP | 0 962 663 A2 | 12/1999 |
| EP | 1 059 458 A2 | 12/2000 |
| WO | WO 01/36085 A1 | 5/2001 |

OTHER PUBLICATIONS

A. Van Den Berg, et al, "Modular Concept for Miniature Chemical Systems", Dechema Monographs, Berlag Chemie, Weinheim, DE, vol. 132 (1996), pp. 109–123.

* cited by examiner

Primary Examiner—Joseph Drodge
(74) Attorney, Agent, or Firm—Sughrue Mion, PLLC (57) ABSTRACT

A system for automated treatment of fluids having interchangeable process modules (39, 40, 41, 42, 43), which are arranged next to each other, and which are respectively provided with a control unit and a fluid unit. The fluid unit is controlled by the control unit in order to carry out a module-specific process function during the treatment of the fluids. The control units are interconnected via a data bus (48), which is common to the process modules (39, 40, 41, 42, 43), and the fluid units are interconnected by a fluid bus (49) that has several channels. A fluid bus section is provided for at least one part of the channels inside each process module (e.g., 42). This section has fluid bus interfaces (52) at the ends thereof. A connection unit (51) is configured to be mounted between the respectively adjacent fluid bus interfaces (52) of two successive process modules (e.g., 41, 42) in at least two different mounting positions. The connection unit (51) connects channel sections that terminate at the adjacent fluid bus interfaces (52) of both process modules (41, 42) in a series of different configurations.

11 Claims, 6 Drawing Sheets

FIG. 1

5- Control Unit
6- Fluid Unit
9- Control Elements
20- Reactor
22- Control Unit
24- Detection Means 25- Common Carrier
26- External Power Supply Source
30- Fluid Bus Connector
32- Reservoir
33- Discharge Reservoir

SYSTEM FOR AUTOMATED TREATMENT OF FLUIDS HAVING SUCCESSIVE AND INTERCHANGEABLE PROCESS MODULES

This is a Continuation of International Application PCT/DE02/00504, with an international filing date of Feb. 12, 2002, which was published under PCT Article 21(2) in German, and the disclosure of which is incorporated into this application by reference.

FIELD OF AND BACKGROUND OF THE INVENTION

The invention relates to the automated treatment of fluids having successive and interchangeable process modules.

Such a system is subject of German patent application DE 199 54 855.2.

United States patent U.S. Pat. No. 5,083,364 discloses a system for producing semiconductor substrates, which includes multiple successive process modules. The process modules are supplied with data, energy, necessary chemicals, gases, and liquids via a common media bus. The media bus is also used to discharge the fluids. At least one of the process modules is configured for supplying the fluids to and discharging the fluids from the fluid bus. The media bus has electric lines for data and power transmission and various pipes for the different fluids. Along the media bus, coupling boxes having electrical fluid terminals are provided at a grid spacing that is defined by the size of the process modules. The individual process modules can be connected to the electrical and fluid terminals by means of respective counter-terminals. The fluid terminals are equipped with self-closing valves, which seal the respective fluid terminal toward the outside if a process module is not connected to the respective counter-coupling. Therefore, in the prior art system, it is relatively simple to add, remove or interchange individual process modules as needed.

The fluid bus of the prior art system is configured specifically for the fluids that are required for producing semiconductor substrates. The prior art system has various pipes for these fluids, which, in part, have different diameters and cross sections. The variability and applicability of the prior-art system is therefore limited to this special production process.

European Patent Application EP-A-0 303 565 discloses a system for producing a, in particular, chemical product. The various production steps are carried out in different fixed or mobile process modules, each of which includes a control unit and a chemical unit. Therein, a respective production step is carried out within the chemical unit under the control of the control unit. The control units of the different process modules are connected to a process control system via data lines. The substances required by or obtained in the production process are individually supplied to or discharged from the chemical units within the process modules via supply and discharge lines. Thus, the desired modularity and flexibility is essentially provided on the control side but not on the process side.

OBJECTS OF THE INVENTION

It is one object of the invention to provide a system for the automated treatment of fluids having a modularity and, therefore, flexibility that is as great as possible.

SUMMARY OF THE INVENTION

According to one formulation of the invention, this and other objects are achieved by a system for automated treatment of fluids having interchangeable process modules that are arranged next to each other. Each of these process modules has a control unit and a fluid unit, which can be controlled by the control unit, to carry out a module-specific process function during the treatment of the fluids. The control units are interconnected via a data bus that is common to the process modules. The fluid units are interconnected via a fluid bus that has a plurality of channels. A least some of the channels within each process module have a respective fluid bus section, at the end of which fluid bus interfaces are arranged. A connection unit can be mounted in at least two different mounting positions between the respectively adjacent fluid bus interfaces of two successive process modules. In the at least two different mounting positions, the connection unit interconnects in differing connection patterns the channel sections that terminate respectively at the adjacent fluid bus interfaces of the two process modules.

The term "treatment of fluids" includes, in particular, the analysis or synthesis of fluids, including the subsidiary functions required therefor. The fluids can be liquids, gases, or solids that are transported by means of carrier fluids. The process modules are selected in accordance with the process functions that are to be carried out within the process and are arranged next to each other in a suitable sequence. The channel sections of adjacent process modules of at least some of the channels of the fluid bus can be interconnected in a predefined connection pattern by mounting a connection unit between them. Depending on its mounting position, the connection unit can be used to configure at least two differing connection patterns. This ensures the greatest possible modularity and flexibility of the system according to the invention not only on the control side but also on the process side, since, in contrast to the prior art systems, there is no fixed pre-allocation of the channels. Because one and the same connection unit can be used to configure differing connection patterns between the channel sections of adjacent process modules, only one or only a few different basic types of connection units are necessary in order to individually interconnect the process modules on the fluid side. These process modules are needed to build different systems.

Particularly for those channels that conduct the fluids to be treated during the process (including educts, products and fluids to be analyzed), it is necessary to individually interconnect the channels of the fluid bus between adjacent process modules. However, other fluids, particularly supply fluids, such as water, coolant, nitrogen, oxygen or compressed air, are usually simultaneously required by all the process modules. As a result, the fluid bus sections in the process modules, which can be connected in different configurations via the connection units, are preferably formed only for one part of the channels of the fluid bus. For the remaining channels of the fluid bus in the process modules, an additional fluid bus section is provided in such a way that, when the process modules are arranged next to each other, the channel sections of these additional fluid bus sections can be interconnected directly, thereby bypassing the connection units mounted between them. This limits the number of the channel sections that can be individually connected between the process modules to the necessary extent. Thereby, the number of different, necessary connection patterns and, thus, the number of the different, necessary basic types of connection units is reduced. The individually interconnectable channel sections of the fluid bus are preferably all alike. This prevents channel sections with different channel diameters from being connected with each other, for example. The remaining channels, which are formed by directly connecting the channel sections in the process modules and which bypass the connection units, can have different channel diameters and/or channel wall materials, depending on the fluid passing through them.

In a preferred embodiment of the system according to the invention, the fluid bus interfaces are formed on the sides of the process modules that face each other when the process modules are arranged next to each other. Therein, the connection unit is mounted between the process modules. It is one substantial advantage of this embodiment that the system is entirely constructed by arranging process modules and connection units next to each other. This makes it possible to use uniform mounting techniques throughout, which results in a simple and functionally reliable structure of the system. In addition, the arrangement of the process modules and the connection units mounted therebetween largely corresponds to the logic structure of the process, so that the user can easily construct the system in a fail-safe manner based on process diagrams or the like. If the channel sections of successive process modules are to be connected with each other in a parallel connection pattern, the two process modules may be directly connected, without an interposed connection unit. Conversely, two or more connection units can be series-connected between two process modules in order to obtain a new composite connection pattern from the connection patterns of the connection units involved. Thus, the number of necessary, basic types of connection units can be further reduced down to a single basic type having four mounting positions or connection patterns, for example. Therein, up to 16 connection patterns can be realized by employing two series-connected connection units.

In an alternative, exemplary embodiment of the system according to the invention, the fluid bus interfaces are formed on the sides of the process modules that are flush when the process modules are arranged next to each other. The connection unit can then be mounted on these sides so as to bridge two successive process modules. This embodiment is particularly advantageous if the process modules are mounted in a predefined grid, for example on a base plate, and if interposed connection units would change or interfere with the grid spacing of the process modules. Furthermore, all of the process modules can be mounted first, and the connection units can be mounted thereafter. Therein, the connection units can be subsequently interchanged, without individual process modules having to be removed.

Preferably, in order to facilitate the construction of the system and to detect structural errors quickly, the connection unit has an information field for each possible mounting position so as to display the connection pattern configured by the respective mounting position. In each mounting position of the connection unit, the associated information field assumes one and the same position. Thus, the user can readily see the configured connection pattern. Additional information fields, which are formed on the process modules and which display their process functions, may be provided on a viewing plane, which is common with the information fields of the connection units that display the configured connection patterns. The individual displays of the different information fields thus provide an overview of the constructed system and complement each other to form, for example, a process diagram.

In a further exemplary embodiment of the system according to the invention, the connection unit, which has a respective mounting position, can be inserted into a holding device. This holding device has a detector to detect the respective mounting position. The detector can be connected to the data bus in order to transmit information indicating the respective mounting position. Thereby, a higher-level control unit, which is connected to the data bus, automatically obtains all the essential information on the structure of the system, including the fluid bus connections between the individual process modules. Based on this information, the higher-level control unit can, e.g., visualize the structure of the system, automatically detect structural errors, and control the process flow in the system. The holding device for the connection unit can be formed on the process modules. As an alternative, the holding device, together with the connection unit inserted therein, forms a connection module, which can be inserted between the process modules when they are arranged next to each other. In the first case, the holding device is formed, for example, by recesses on the process modules that are adapted to receive and hold the connection units. The detector are integrated in the process modules, e.g., as a component of their control units. In the case of the connection modules, these modules have preferably the same basic structure as the process modules. Here, the connection unit and the detector in the connection modules correspond to the fluid unit or the control unit in the process module. A data bus section may be formed within the holding device, which, together with data bus sections in the adjacent process modules, forms the data bus. Furthermore, for the remaining channels of the fluid bus, additional fluid bus sections may be provided within the holding device, which are not to be connected via the connection unit. When the connection module is inserted between two process modules, this fluid bus section connects the channel sections of the additional fluid bus sections contained in these process modules.

BRIEF DESCRIPTION OF THE DRAWINGS

Exemplary embodiments of the invention will now be described in greater detail with reference to the drawings, in which.

DETAILED DESCRIPTION OF THE PREFERRED EMBODIMENTS

Figure 1:
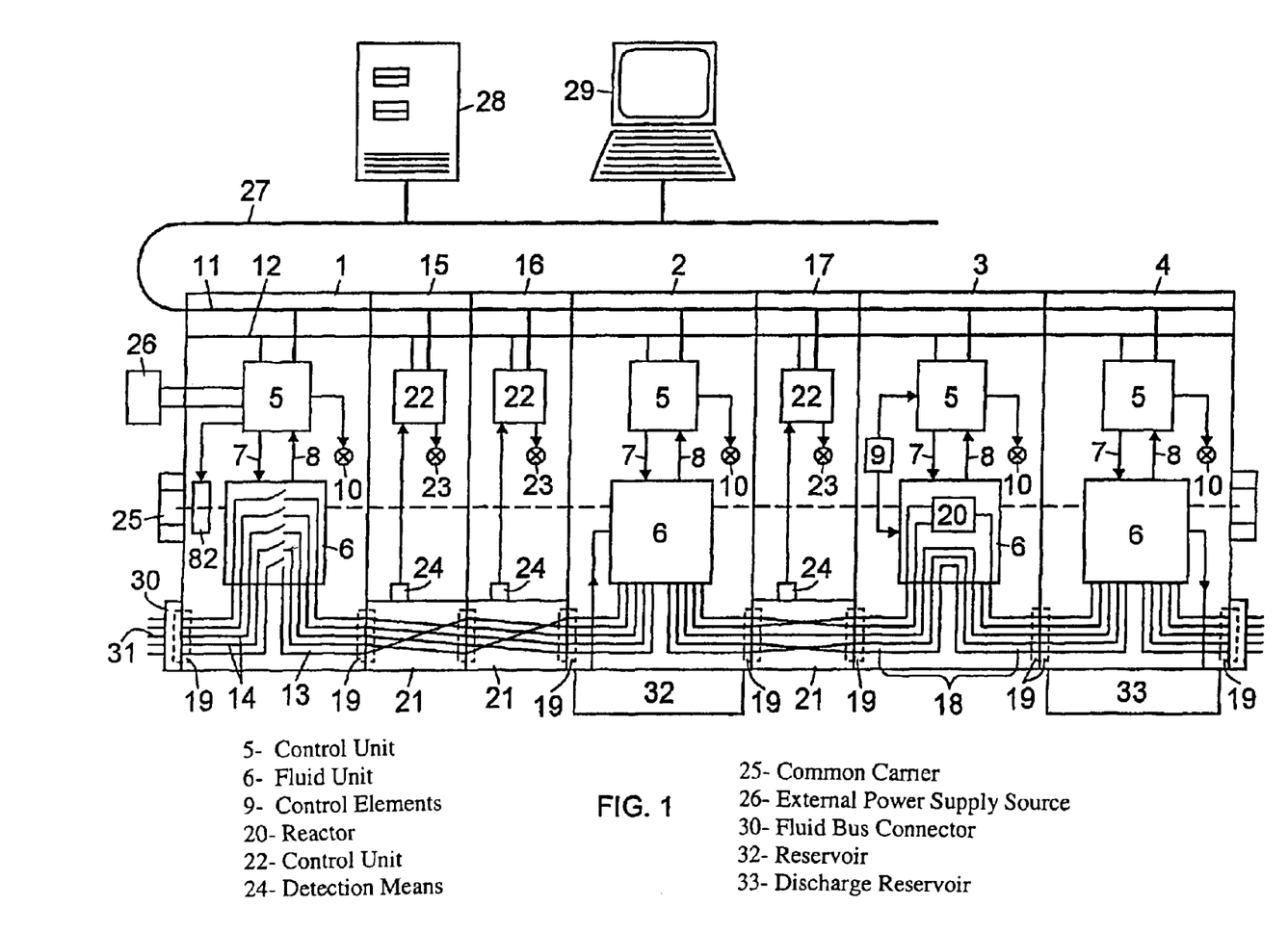
FIG. 1 is a simplified block diagram illustrating an exemplary embodiment of the system according to the invention and including different process modules.

FIG. 1 shows a system for the automated treatment of fluids, e.g., different liquids or gases. The term "treatment" should be understood as, for example, analyzing fluids and/or synthesizing fluids by chemical reactions, including necessary required subsidiary functions, such as preparing, mixing, filtering, transporting or building up pressure via pumps, heating, evaporation, etc. The system includes different, successive process modules 1, 2, 3 and 4, in which module-specific process functions are carried out automatically. In accordance with the aforementioned treatment functions, the process modules 1 to 4 can be various kinds of analysis modules; reactor modules having, e.g., microreactors; pump modules; filter modules; power supply modules; fluid supply and fluid discharge modules; etc. Each process module 1 to 4 has a control unit 5 and a fluid unit 6. The actual process or treatment function is carried out within the fluid unit 6 as a function of control signals 7 from the control unit 5. Process signals 8, e.g., pressure values or analysis values, detected in the fluid unit 6 are transmitted to the control unit 5. As shown, by way of example, in the process module 3, control elements 9 may be provided on the individual process modules to adjust the control unit 5 and/or the fluid unit 6. Further, the process modules 1 to 4 have display elements 10, which are controlled by the control units 5 to display operating states and/or error conditions.

The control units 5 in the different process modules 1 to 4 are interconnected via a data bus 11 and a power supply bus 12. The fluid units 6 are interconnected via a fluid bus 13, which includes a plurality of channels 14 that carry the respectively required fluids. The data bus 11, the power supply bus 12, and the fluid bus 13 are each composed of bus sections that extend within the successive process modules 1 to 4 and within connection modules 15, 16 and 17. Therein, bus interfaces are provided at the ends of the bus sections. For example, the fluid bus sections 18 in the process modules each have two fluid bus interfaces 19 at their ends. These fluid bus interfaces are formed on the sides of the process modules that are facing each other when the process modules are arranged next to each other. Within the process modules, the channel sections of the fluid bus section 18 can run differently depending on the process function. For example, the fluid unit 6 of the process module 3 contains a reactor 20 with two input channels and one output channel. The remaining channels of the fluid bus section 18 run parallel between the fluid bus interfaces 19, so that the fluids conducted therein reach the next process module 4 in an uninfluenced manner.

In the case of the directly adjoining process modules 3 and 4, the channel sections terminating at the adjacent fluid bus interfaces 19 of the two process modules 3 and 4 are directly interconnected. In contrast, in the process modules 1, 2 and 3, the channel sections of the successive process modules 1 and 2 or 2 and 3 are interconnected individually according to predefined connection patterns. This is accomplished via connection units 21, which are mounted between the fluid bus interfaces 19 of the successive process modules 1 and 2 or 2 and 3, and which establish the respective connection pattern. Therein, the connection units 21 are a component of the connection modules 15, 16 and 17, which are arranged between the process modules 1 and 2 or 2 and 3 when the process modules 1 to 4 are aligned. Similarly to the process modules 1 to 4, each connection module 15 to 17 includes a control unit 22, which is connected to the data bus 11 and the power supply bus 12. The control unit 22 controls display elements 23 disposed on the connection module 15 to 17 and receives information from a detector 24 regarding the connection pattern configured by the connection unit 21. As will be explained in greater detail below, the connection unit 21 can be switched to at least two different mounting positions between the respectively adjacent fluid bus interfaces 19 of two successive process modules, e.g., 2 and 3. In these mounting positions, the connection unit 21 interconnects the channel segments, which respectively terminate at the adjacent fluid bus interfaces 19 of the two process modules 2 and 3, in differing connection patterns. Furthermore, as will also be explained in greater detail below, the different fluid bus sections 18 in the process modules 1 to 4, which can be differently connected via the connection units 21, may contain only part of the channels of the entire fluid bus 13. By bypassing the interposed connection units 21, the remaining channels may be interconnected directly.

The process modules 1 to 4 and the connection modules 15 to 17 mounted therebetween are supported side by side on a common carrier 25, such as, as in this case, a top hat rail, for example. The buses 11 to 13 are formed by sliding or attaching the process modules 1 to 4 and the connection modules 15 to 17 onto the top hat rail 25, as needed.

The process modules 1 to 4 can have other, external terminals in addition to the connections with the data bus 11, the power supply bus 12 and the fluid bus 13. In the exemplary embodiment shown, the process module 1 provides basic functions for the system. For this purpose, the control unit 5 is connected to an external power supply source 26 and, via a data connection, e.g., an external bus 27, to a higher-level control unit 28, e.g., a control system with an operating and visualization unit 29. As an alternative, a battery or fuel cell module may be used for the power supply. External fluid lines 31 for supplying or discharging the required fluids to and from the system can be connected via a fluid bus connector 30 provided on the fluid bus 13. The fluid unit 6 can control the routing of the fluids to the following process modules 2 to 4, for example. In the process module 2, a fluid is fed into the system via a reservoir 32 that can be attached to the process module 2. A discharge reservoir 33 for receiving a fluid from the system is connected, for example, to the process module 4.

The control units 5 in the process modules 1 to 4 control the module-specific process functions. Therein, the control units 5 receive instructions from and transmit process information to the higher-level control unit 28. In addition, the control units 5, like the control units 22, in the connection modules 15 to 17, signal the selection, arrangement, and interconnection of the modules 1 to 4 and 15 to 17 to the higher-level control unit 28. The higher-level control unit 28 uses this information to visualize the structure of the system and to automatically detect structural errors. Structural errors can also be displayed directly via the display elements 10 and 23 on the modules 1 to 4 and 15 to 17. In addition, the higher-level control unit 28 can identify all the used modules 1 to 4 and 15 to 17 by means of serial numbers that are assigned to each individual module during manufacture. This ensures, for example, that the same modules 1 to 4 and 15 to 17 are used each time the same process flows are repeated.

For safety reasons, during the course of the process in the system, the modules 1 to 4 and 15 to 17 are mutually mechanically locked on the carrier 25 by a locking mechanism 82 that can be automatically actuated. When prompted by the higher-level control unit 28, the lock is canceled by the control units 5 and 22 in the modules 1 to 4 and 15 to 17 when the process has been completed in the system and the channels 14 and other fluid-carrying parts of the system have been purged using a cleaning fluid, if necessary. Alternatively, as shown here, the lock is canceled by the control unit 5 of the process module 1 for all the modules 1 to 4 and 15 to 17.

Figure 2:
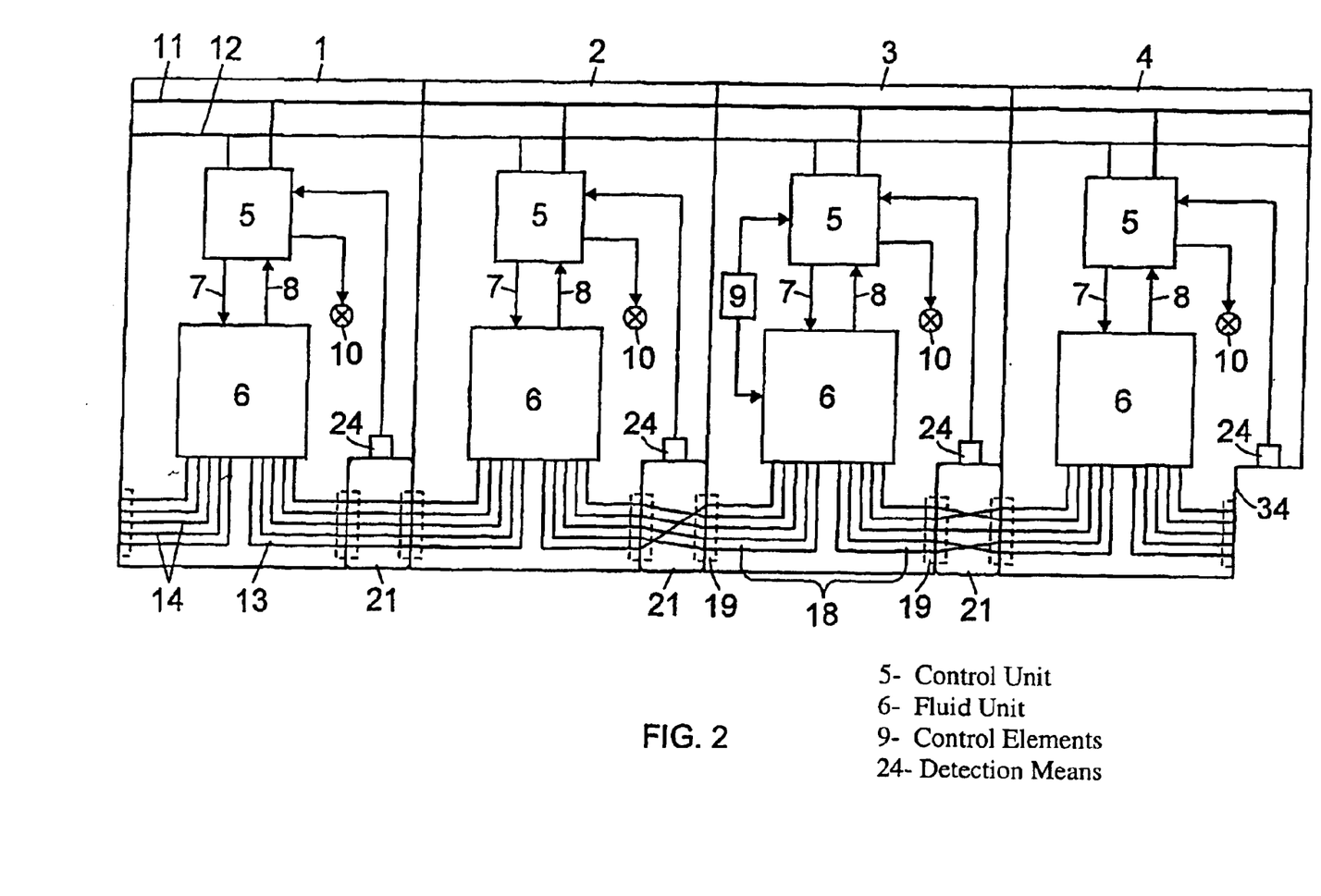
FIG. 2 is a variant of the exemplary embodiment depicted in FIG. 1.

The system shown in FIG. 2 for the automated treatment of fluids is distinguished from that of FIG. 1 in that the process modules 1 to 4 are directly arranged next to each other, i.e., without interposing the connection modules. The process modules 1 to 4 themselves are provided with receiving devices 34, for example in the form of recesses, to receive the connection units 21. The detector 24 for detecting the respective connection unit 21 is a component of the respective process module 1 to 4, whose control unit 5 transmits information regarding the connection pattern configured with the connection unit 21 to the higher-level control unit 28 (FIG. 1).

Figure 3:
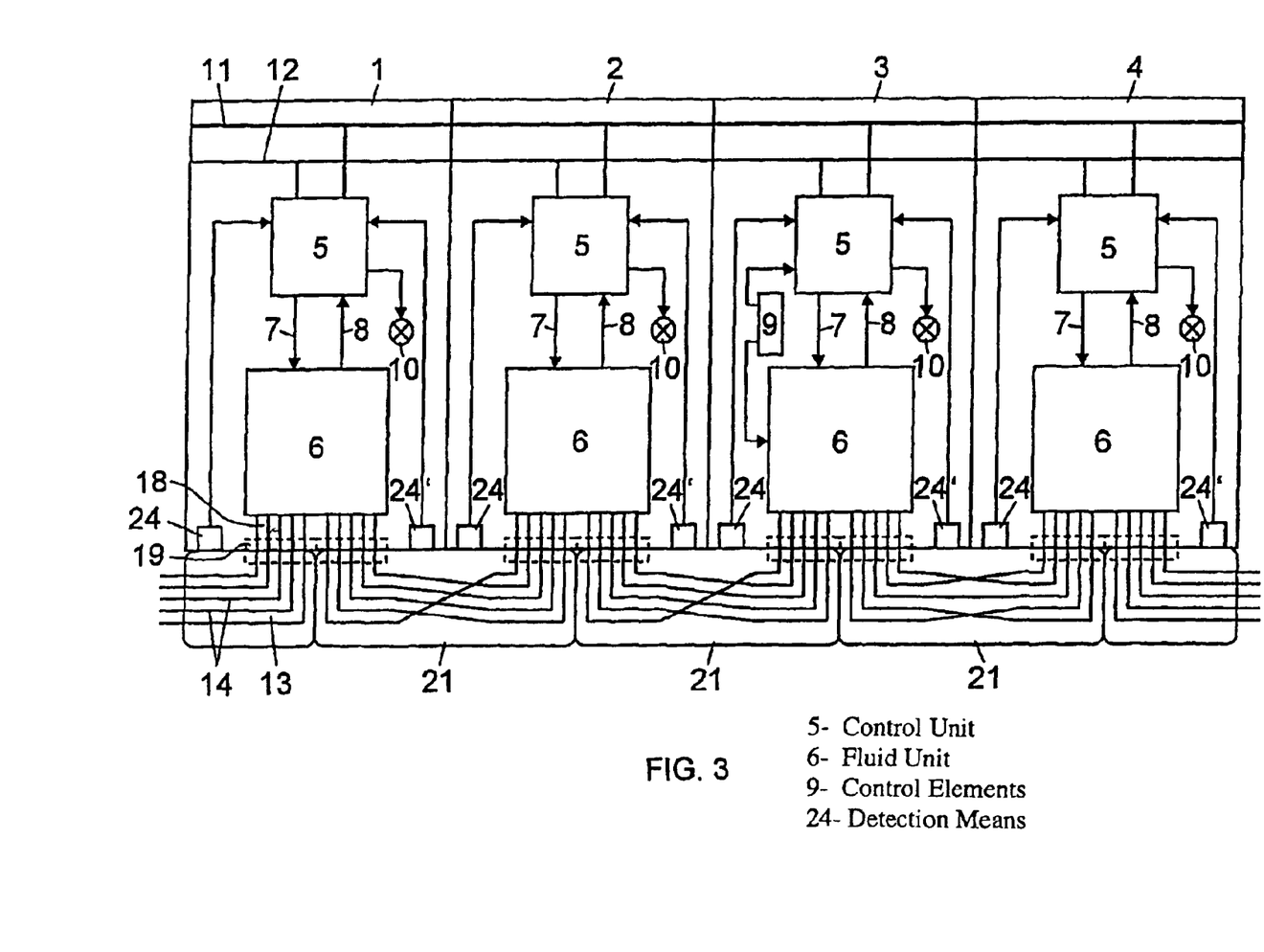
FIG. 3 is a further variant of the exemplary embodiment depicted in FIG. 1.

In contrast to the above-described exemplary embodiments, the fluid bus interfaces 19 in the system for the automated treatment of fluids shown in FIG. 3 are not formed on the sides of the process modules 1 to 4 that are facing each other when the modules are aligned but on the flush sides of the process modules 1 to 4. The connection units 21 are mounted on these sides so as to bridge two successive process modules 1 and 2, 2 and 3, 3 and 4. Here, too, the detectors 24 and 24' for detecting the respective connection unit 21 are components of the respective process module 1 to 4, whose control unit 5 transmits information regarding the connection pattern configured with the connection unit 21 to the higher-level control unit 28 (FIG. 1).

The structural configuration of the system according to the invention will now be described with reference to additional exemplary embodiments. According to the process diagram shown in FIG. 4, four fluids A, B, C and D are to be mixed and subsequently processed into a product E in the presence of pressure and heat. For this purpose, the fluids A, B, C and D are successively combined in three mixers 35, 36 and 37. The mixture thus obtained then goes through a dwell cycle 38 at a predefined pressure and at a predefined temperature.

Figure 4:
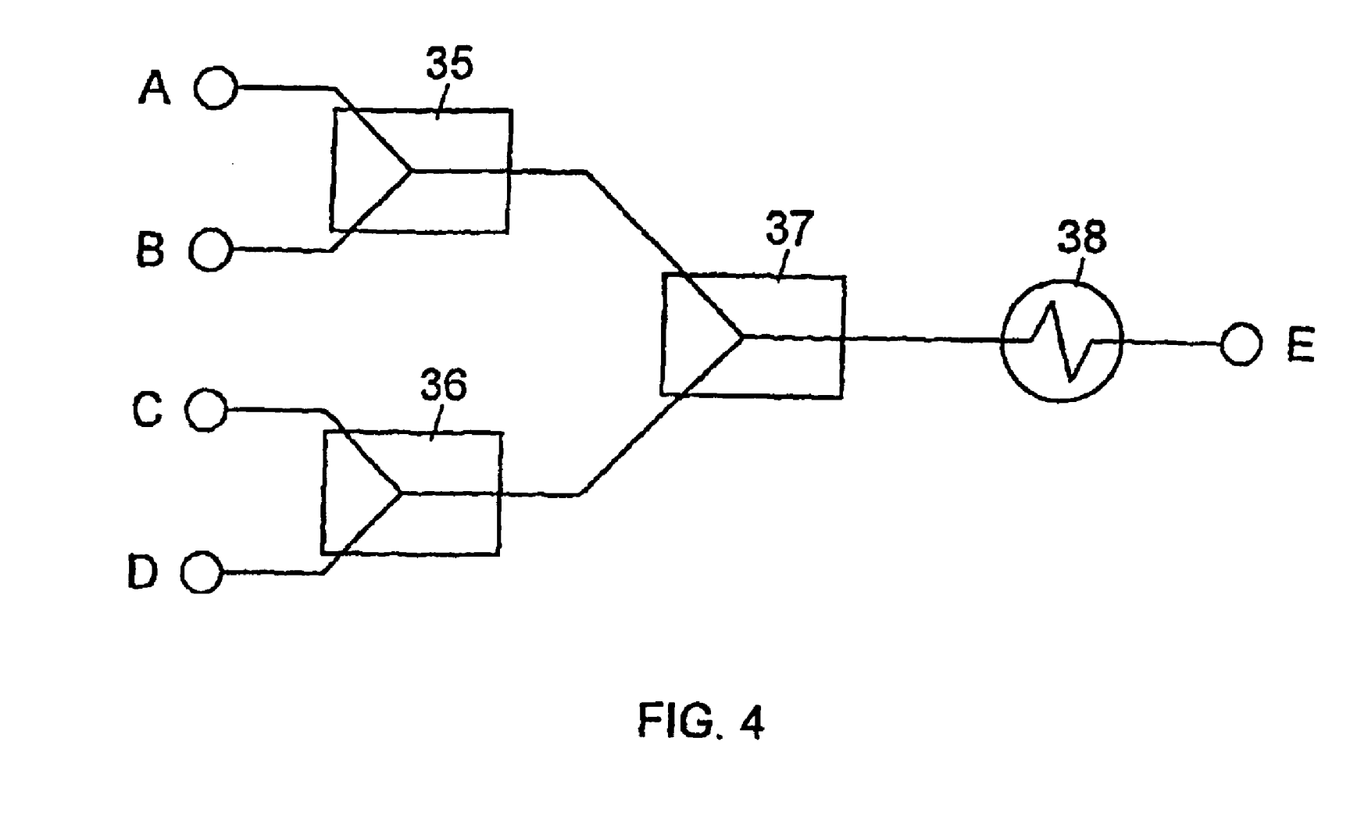
FIG. 4 is a process diagram illustrating an exemplary, simple process.
Figure 5:
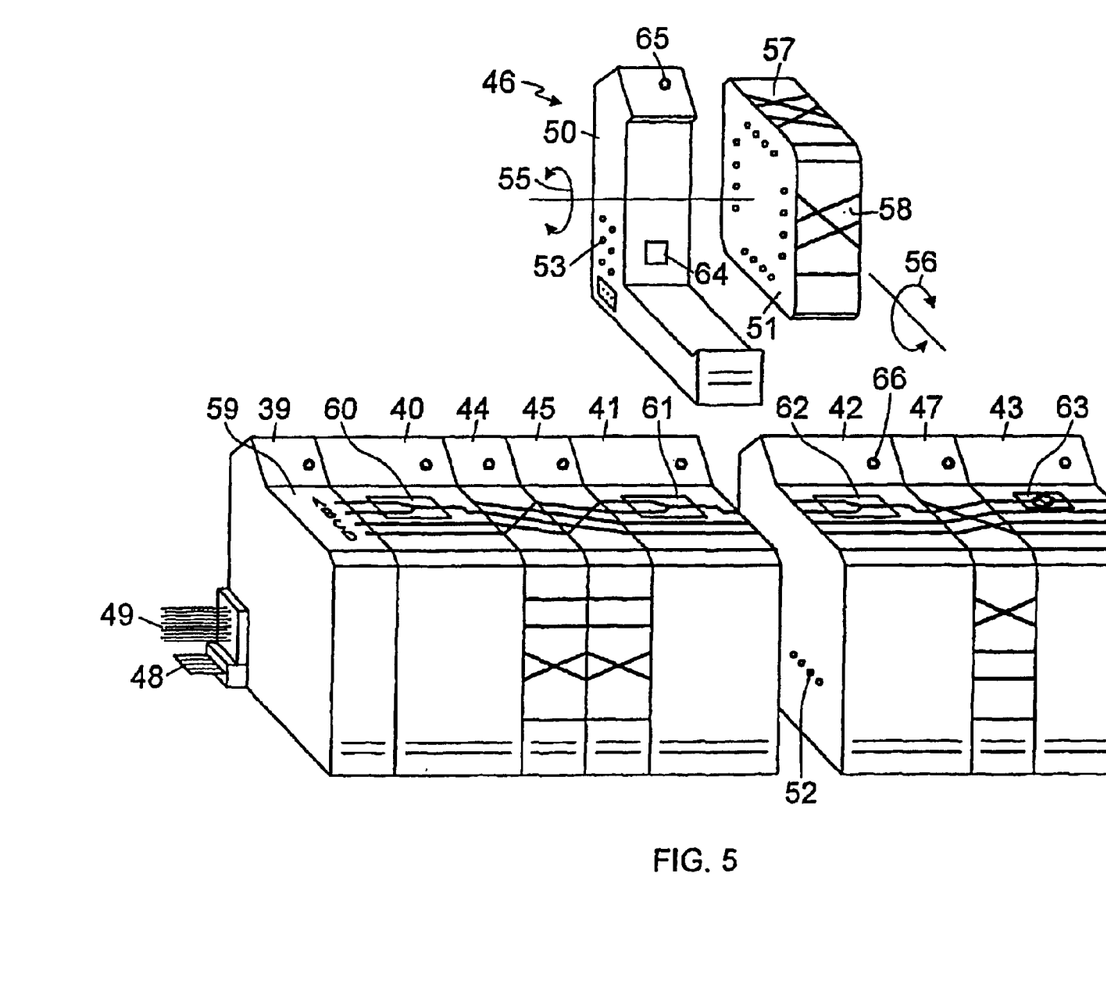
FIG. 5 is a simplified perspective view of an exemplary embodiment of the system according to the invention, which is built in accordance with the process diagram depicted in FIG. 4.

FIG. 5 shows an exemplary structure of the system according to the invention that is built in accordance with the process diagram shown in FIG. 4. The exemplary embodiment of the system includes a supply module 39 to supply the fluids A, B, C and D; three identical mixer modules 40, 41 and 42; and a dwell cycle module 43. The process modules 39 to 43 are successively arranged next to each other with connection modules 44, 45, 46 and 47 mounted therebetween. In accordance with FIG. 1, a data and power supply bus 48 and a fluid bus 49—in this case, for example, a 10-channel fluid bus—extend through the modules 39 to 47. The connection module 46 that is removed from the row of the modules 39 to 47 shows that each of these connection modules includes a holding device 50 and a connection unit 51 that can be inserted therein.

In particular for those channels that conduct the fluids to be treated in the course of the process, it is necessary to be able to connect the channels of the fluid bus 49 individually between adjacent process modules, e.g., 41 and 42. In contrast, other fluids, in particular supply fluids, such as water, coolant, nitrogen, oxygen or compressed air, are usually simultaneously needed by all the process modules 39 to 43. For four of the 10 channels of the fluid bus 49—in this case, for example, the channels conducting the fluids A, B, C and D—a fluid bus section is formed in each of the process modules 39 to 43, which terminates into a respective fluid bus interface 52 at the sides of the process modules 39 to 43 facing each other when the process modules 39 to 43 are aligned. The fluid bus interfaces 52 are arranged in such a way that, when a connection module, e.g., 46, is inserted between the two process modules 41 and 42, the channel sections of the two process modules 41 and 42 terminating at the fluid bus interfaces 52 are connected with each other by the connection unit 51 of the connection module 46 in a predefined connection pattern.

For the remaining six channels of the fluid bus 49, additional fluid bus sections are formed in the process modules 39 to 43. When the process modules 39 to 43 are aligned or arranged next to each other, these fluid bus sections are interconnected directly by additional fluid bus sections 53 formed in the holding devices 50 of the interposed connection modules 44 to 47 and thus bypass the connection units 51. Likewise, a data and power supply bus section is formed within each holding device 50, which, together with the bus sections in the adjacent process modules, e.g., 41 and 42, forms the data and power supply bus 48.

As indicated by arrows 55 and 56, the connection unit 51 can be inserted into the holding device 50 in different mounting positions, so that the channel sections that terminate at the adjacent fluid bus interfaces 52 of the two process modules 41 and 42 are interconnected in differing connection patterns, depending on the mounting position. The connection unit 51 carries an information field 57, 58 for each possible mounting position so as to display or indicate the connection pattern that can be configured in this position. The information field, e.g., 57, which, in the current mounting position of the connection unit 51, shows the connection pattern formed in this position, lies in a common viewing plane together with other information fields 59, 60, 61, 62 and 63. These other information fields 59, 60, 61, 62 and 63 are formed on the process modules 39 to 43 and display or indicate their process functions. As a result, the individual displays or indications of the different information fields complement each other to form a display of the overall process diagram. The holding device 50 has a detector 64, which detects the respective mounting position of the connection unit 51 by mechanical, electrical or optical scanning of a code on the connection unit 51 and transmits the associated information regarding the connection pattern that is currently configured with the connection unit 51 to the data bus 48, as described above with reference to FIG. 1. If a higher-level control unit that is connected to the data bus 48 detects an incorrectly configured connection pattern, then this information is signaled to the associated connection module 46 and displayed there by means of a display element 65. Likewise, the process modules 39 to 43 are equipped with display elements 66 for displaying any errors.

Figure 6:
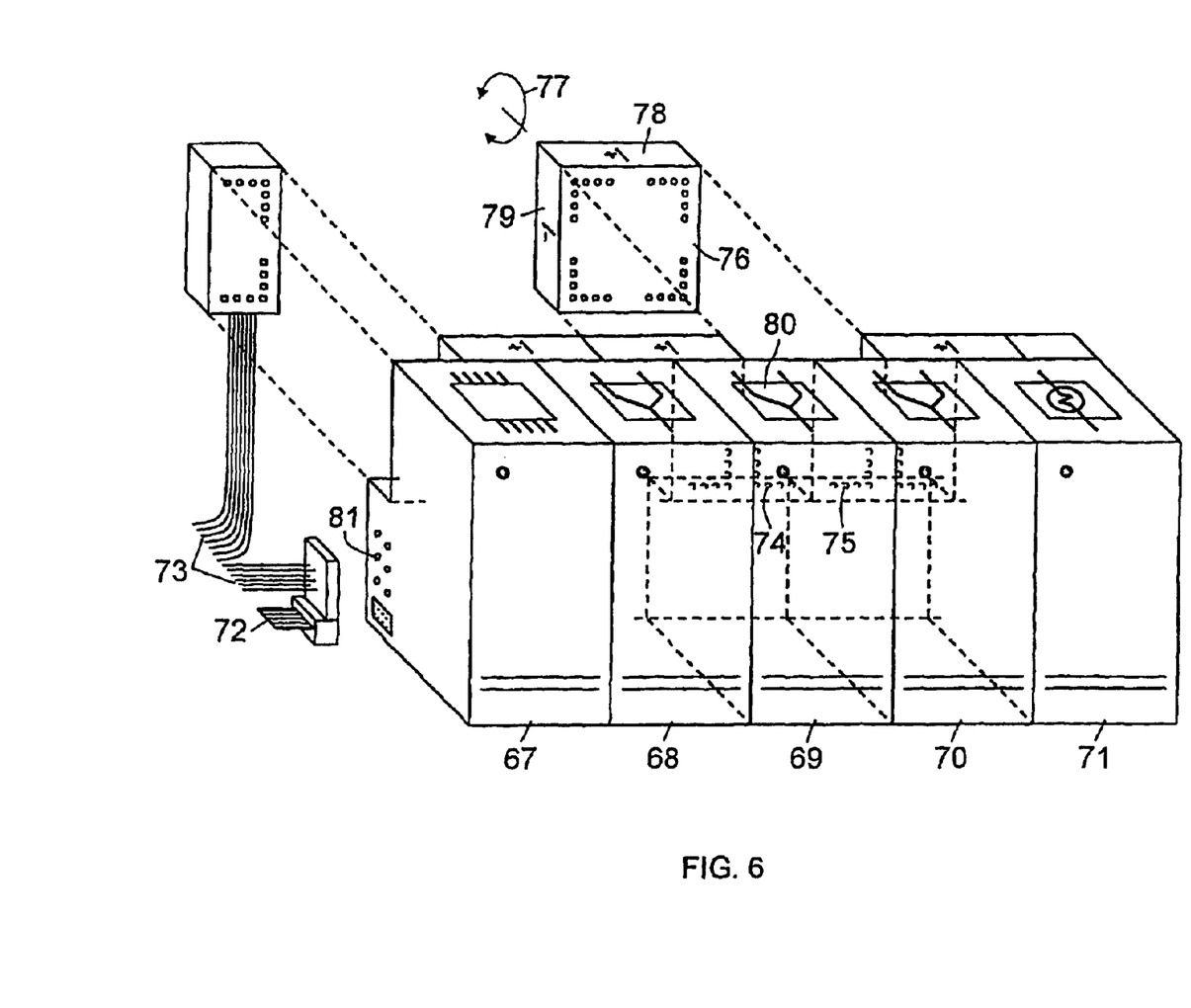
FIG. 6 is a variant of the exemplary embodiment depicted in FIG. 5.

In the exemplary embodiment of the system according to the invention shown in FIG. 6, process modules 67, 68, 69, 70 and 71 are arranged directly adjacent to each other. In accordance with the illustration in FIG. 3, a data and power supply bus 72 and a multi-channel fluid bus 73 run through the process modules 67 to 71.

For a predefined number of channels of the fluid bus 73, a respective fluid bus section that is provided with fluid bus interfaces at its two ends is formed in each process module 67 to 71. When the process modules 67 to 71 are arranged next to each other, these fluid bus interfaces are formed on the flush rear sides of the process modules 69 and 70. The channel sections of two successive process modules—here, e.g., 69 and 70—which terminate at fluid bus interfaces 74 and 75, are connected with each other by a connection unit 76 in a predefined connection pattern. For this purpose, the connection unit 76 can be mounted to the rear sides of the process modules 69 and 70 so as to bridge these modules. As indicated by an arrow 77, the connection unit 76 can be mounted on the rear sides of the process modules 69 and 70 in different mounting positions, so that the channel sections terminating at the adjacent fluid bus interfaces 74 and 75 of the two process modules 69 and 70 are connected with each other in differing connection patterns, depending on the mounting position. The connection unit 76 carries an information field 78, 79 for each possible mounting position to show the connection pattern that can be configured in each position. The information field, e.g., 78, which, in a respective mounting position of the connection unit 76, indicates the connection pattern configured in this position, lies in a common viewing plane together with other information fields 80 that are formed on the process modules 67 to 71 and that display their process functions.

For the remaining channels of the fluid bus 73, additional fluid bus sections are formed in the process modules 67 to 71, which terminate at additional fluid bus interfaces 81 on the sides of the process modules 67 to 71 that face each other. When the process modules 67 to 71 are arranged next to each other, these fluid bus sections are directly interconnected and, thus, bypass the connection units, e.g., 76. Likewise, the data and power supply bus sections formed within the process modules 67 to 71 complement each other to form the data and power supply bus 72.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A system for automatically treating fluids, comprising:
    a plurality of interchangeable, successive process modules, each process module comprising:
        a control unit; and
        a fluid unit controlled by the control unit, wherein the fluid unit is configured to carry out a module-specific process function in the course of automatically treating the fluids;
    a data bus, which is common to the process modules and which interconnects the respective control units of each process module;
    a fluid bus comprising a plurality of channels, which interconnects the respective fluid units of each process module, wherein a predefined number of the channels comprises respective fluid bus sections within the process modules, and wherein the respective fluid bus sections have fluid bus interfaces at the ends of the respective fluid bus sections; and
    a connection unit mounted between adjacent ones of the fluid bus interfaces of two successive ones of the process modules, wherein the connection unit is configured to be mounted in at least two different mounting positions, in accordance with which the connection unit is configured to connect channel sections terminating at the adjacent ones of the fluid bus interfaces in respective, differing connection patterns.

2. The system as claimed in claim 1,
    wherein the predefined number of the channels comprising the respective fluid bus sections is less than a total number of the plurality of channels of the fluid bus;
    wherein the remaining channels of the fluid bus comprise a respective, further fluid bus section; and
    wherein further channel sections of the respective, further fluid bus section are directly connected, thereby bypassing the connection unit.

3. The system as claimed in claim 2, further comprising:
    a holding device into which the connection unit is inserted so as to form a connection module;
    wherein the remaining channels of the fluid bus within the holding device comprise an additional fluid bus section, which, when the connection module is inserted between two of the process modules, connects the further channel sections of the further fluid bus sections contained in the two process modules.

4. The system as claimed in claim 1,
    wherein the fluid bus interfaces are formed on sides of the two successive ones of the process modules that face each other; and
    wherein the connection unit is mounted between the two successive ones of the process modules.

5. The system as claimed in claim 1,
    wherein the fluid bus interfaces are formed on flush sides of the successive process modules; and
    wherein the connection unit is mounted on the flush sides so as to bridge the successive process modules.

6. The system as claimed in claim 1,
    wherein the connection unit has a respective information field for each of the at least two different mounting positions;
    wherein the respective information field is configured to indicate one of the respective, differing connection patterns configured by a respective one of the at least two different mounting positions; and
    wherein the respective information field assumes an identical position in each of the at least two different mounting positions.

7. The system as claimed in claim 6, wherein the respective information field is arranged in a common viewing plane together with additional information fields that are formed on the process modules and that display process functions of the process modules.

8. The system as claimed in claim 1, further comprising:
    a holding device into which the connection unit is inserted;
    wherein the holding device has a detector for detecting a respective one of the at least two different mounting positions; and
    wherein the detector is connected to the data bus for transmitting information indicating the respective one of the at least two different mounting positions.

9. The system as claimed in claim 8, wherein the holding device is formed on the process modules.

10. The system as claimed in claim 8, wherein the holding device and the connection unit inserted into the holding device form a connection module that is inserted between the process modules.

11. The system as claimed in claim 10, wherein the holding device has a data bus section, which, together with further data bus sections in adjacent ones of the process modules, forms the data bus.

* * * * *